US010781417B2

(12) United States Patent
Purushothaman et al.

(10) Patent No.: US 10,781,417 B2
(45) Date of Patent: Sep. 22, 2020

(54) SYSTEM AND METHOD FOR DETACHMENT OF CELLS IN FIXED BED REACTORS

(71) Applicants: PALL TECHNOLOGY UK LIMITED, Portsmouth (GB); PALL LIFE SCIENCES BELGIUM, Hoegaarden (BE); PALL ARTELIS BVBA, Brussels (BE)

(72) Inventors: Suresh Purushothaman, Leuven (BE); Jose Antonio Castillo Gonzalez, Brussels (BE); Jean-Christophe Drugmand, Louvain-la-neuve (BE); Vishwas Pethe, Shakopee, MN (US); Derek Pendlebury, Meriden, CT (US); Fabien Moncaubeig, Edina, MN (US)

(73) Assignees: PALL TECHNOLOGY UK LIMITED, Portsmouth (GB); PALL ARTELIS BVBA, Hoegaarden (BE); PALL LIFE SCIENCES BELGIUM B.V.B.A., Hoegaarden (BE)

( * ) Notice: Subject to any disclaimer, the term of this patent is extended or adjusted under 35 U.S.C. 154(b) by 879 days.

(21) Appl. No.: 14/648,571

(22) PCT Filed: Dec. 11, 2013

(86) PCT No.: PCT/US2013/074298
§ 371 (c)(1),
(2) Date: May 29, 2015

(87) PCT Pub. No.: WO2014/093439
PCT Pub. Date: Jun. 19, 2014

(65) Prior Publication Data
US 2015/0322399 A1    Nov. 12, 2015

Related U.S. Application Data

(60) Provisional application No. 61/735,841, filed on Dec. 11, 2012.

(51) Int. Cl.
C12M 1/00      (2006.01)
C12M 1/26      (2006.01)
(Continued)

(52) U.S. Cl.
CPC ............ *C12M 23/34* (2013.01); *C12M 23/26* (2013.01); *C12M 25/14* (2013.01); *C12M 25/18* (2013.01);
(Continued)

(58) Field of Classification Search
CPC ...... C12M 25/14; C12M 23/34; C12M 25/18; C12M 33/12; C12M 27/12; C12M 29/14;
(Continued)

(56) References Cited

U.S. PATENT DOCUMENTS 4,322,296 A    3/1982   Fan
4,720,462 A    1/1988   Rosenson
(Continued)

FOREIGN PATENT DOCUMENTS

CN    1750868 A     3/2006
CN    101316925 A   12/2008
(Continued)

*Primary Examiner* — Gautam Prakash
(74) *Attorney, Agent, or Firm* — King & Schickli, PLLC

(57) ABSTRACT

An apparatus for processing cells is disclosed. In one embodiment, a fixed bed reactor is provided for the cells, the fixed bed reactor including a portion movable from a first position corresponding to a packed condition of the fixed bed to a second position corresponding to a depacked condition of the fixed bed. Movement of the partition facilitates harvesting of the cells there from. Related apparatus, kits, methods, and systems are also disclosed.

7 Claims, 12 Drawing Sheets

(51) Int. Cl.
*C12M 1/12* (2006.01)
*C12M 3/04* (2006.01)

(52) U.S. Cl.
CPC ............ *C12M 27/12* (2013.01); *C12M 29/14* (2013.01); *C12M 33/08* (2013.01); *C12M 33/12* (2013.01); *C12M 33/14* (2013.01); *C12M 33/18* (2013.01); *C12M 47/02* (2013.01)

(58) Field of Classification Search
CPC ...... C12M 33/18; C12M 33/14; C12M 23/26; C12M 47/02; C12M 33/08
See application file for complete search history.

(56) References Cited

U.S. PATENT DOCUMENTS

| | | | |
|---|---|---|---|
| 5,432,087 A | 7/1995 | Spielmann | |
| 5,527,705 A | 6/1996 | Mussi | |
| 5,707,868 A * | 1/1998 | Boulay et al. | C12M 41/44 435/243 |
| 7,856,704 B2 * | 12/2010 | Wang et al. | B21D 39/031 29/715 |
| 8,137,959 B2 | 3/2012 | Castillo Fernandez | |
| 8,501,430 B2 * | 8/2013 | Schweigert | G01N 1/4055 435/11 |
| 2003/0093034 A1 | 5/2003 | Chang et al. | |
| 2003/0175853 A1 | 9/2003 | Clarke et al. | |
| 2004/0058436 A1 | 3/2004 | Zhang et al. | |
| 2004/0110273 A1 | 6/2004 | Akers et al. | |
| 2004/0159616 A1 | 8/2004 | Cohee et al. | |
| 2007/0072290 A1 * | 3/2007 | Hvichia | B01L 3/502761 435/308.1 |
| 2011/0281343 A1 | 11/2011 | Gay | |
| 2011/0319868 A1 * | 12/2011 | Hiles et al. | A61L 27/24 604/522 |

FOREIGN PATENT DOCUMENTS

| | | |
|---|---|---|
| DE | 102008039812 A1 | 3/2010 |
| JP | 07-506250 | 7/1995 |
| WO | 9209681 A1 | 6/1992 |
| WO | 9519424 A1 | 7/1995 |
| WO | WO2008136371 A1 | 11/2008 |
| WO | 2009139703 A1 | 11/2009 |
| WO | 2011133437 A2 | 10/2011 |
| WO | 2012140519 A2 | 10/2012 |

* cited by examiner

| | Cells on carrier | Cells in detaching solution | | | | | |
|---|---|---|---|---|---|---|---|
| | Before harvest (from trypsin test on single carriers) | After first Rinse A | After second rinse B | After Trypsin C | After mech. action D | After 3 back and forth E | After second Mech action F |
| Cells on carriers (cell/cm2) | 30 200 | NA | NA | NA | NA | NA | NA |
| Volume centrifugated (ml) | NA | 20 | 20 | 20 | 20 | 20 | 20 |
| Final volume (ml) | NA | 0,7 | 0,7 | 0,7 | 0,7 | 0,7 | 0,7 |
| Average Count (alive) | NA | 0 | 0 | 10 | 74 | 62 | 72 |
| Cell concentration in detaching solution (cells/ml) | NA | 0 | 0 | 7 000 | 51 800 | 43 400 | 50 400 |
| Total cells in detaching solution (or bioreactor) | 45.3 | 0 | 0 | 6.72 | 48.7 | 40.8 | 45.4 |
| Percentage of Total cells in bioreactor | 100 | 0 | 0 | 14.8 | 107.5 | 90.1 | 100.0 |

FIG. 8

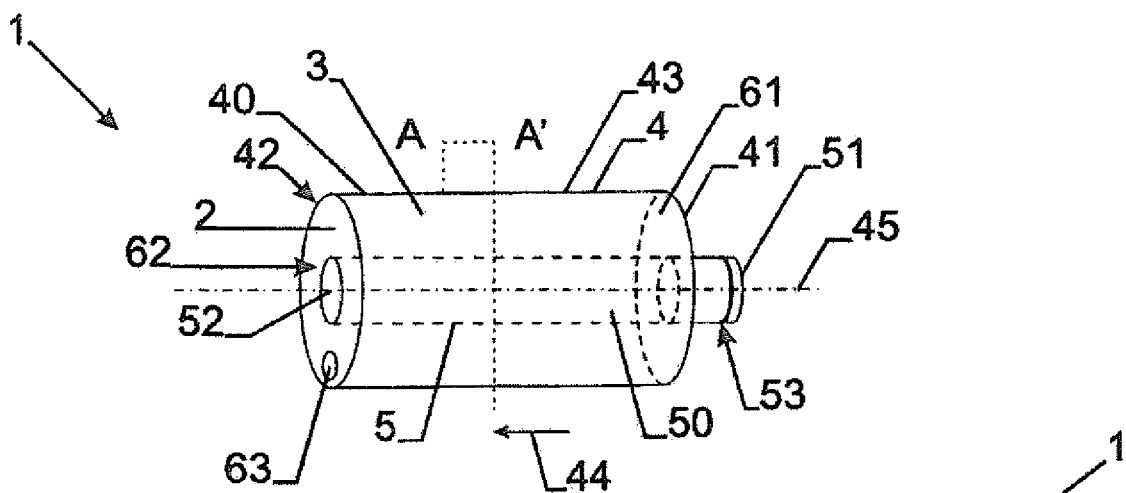
FIG. 10
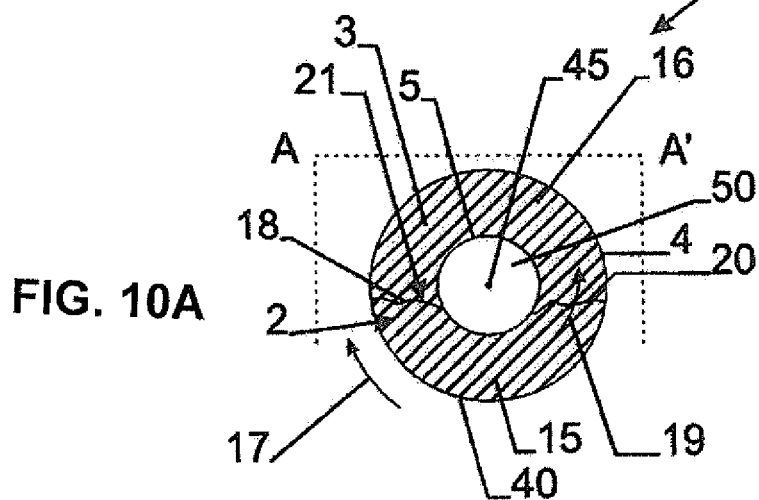
FIG. 10A
FIG. 11
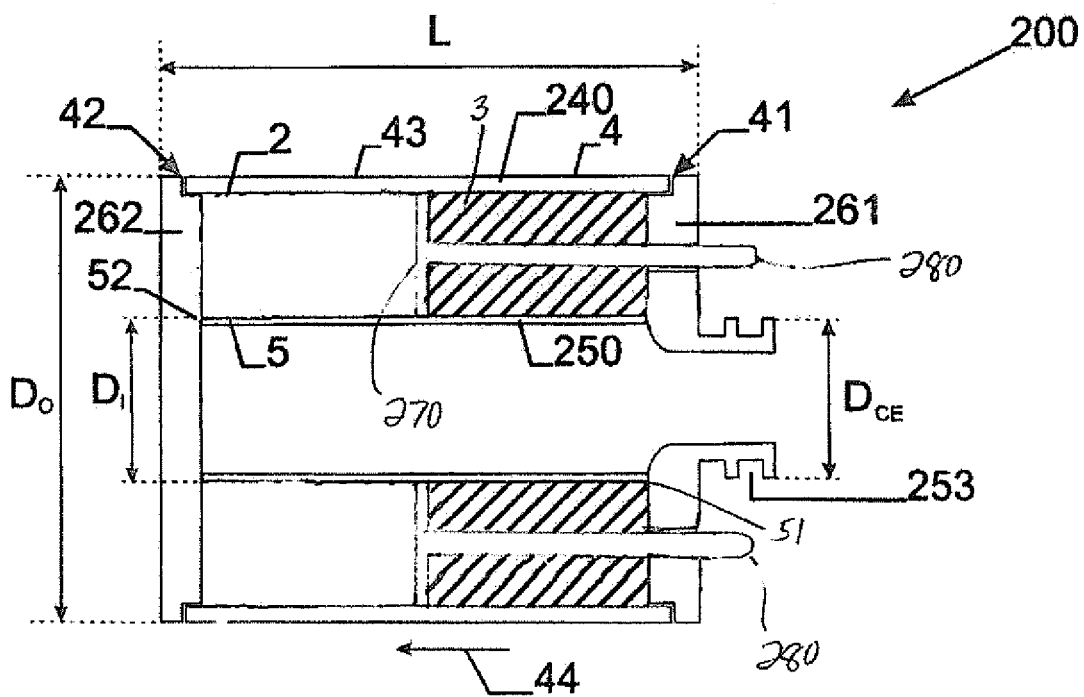

SYSTEM AND METHOD FOR DETACHMENT OF CELLS IN FIXED BED REACTORS

This application claims the benefit of U.S. Provisional Patent Application Ser. No. 61/735,841, the disclosure of which is incorporated herein by reference.

TECHNICAL FIELD

This disclosure relates generally to the bioprocessing arts and, more particularly, to a system and method for the detachment of cells in a fixed bed reactor, apparatus, systems, and kits for bioprocessing, and related methods.

BACKGROUND OF THE INVENTION

Many bioreactors include a carrier in the form of a stationary packing material forming a fixed or packed bed for promoting cell adhesion and growth. The arrangement of the packing material of the fixed bed affects local fluid, heat, and mass transport, and usually is very dense to maximize cell cultivation in a given space. To harvest the cells from the packed or fixed bed, a chemical agent, such as trypsin, may be used, but this alone often causes only a limited amount of cell detachment. The problem, in part, results from the densely packed nature of the fixed bed material in a typical reactor, which makes it more difficult to circulate the chemical agent throughout the bed and increase the yield of cells harvested.

Thus, a need is identified for a manner of improving the yield of cells harvested from a fixed bed reactor.

SUMMARY

In one aspect, an apparatus for processing cells comprises a fixed bed reactor for the cells. The fixed bed reactor includes a portion movable from a first position corresponding to a packed condition of the fixed bed to a second position corresponding to a depacked condition of the fixed bed. Consequently, movement of the partition expands the fixed bed to facilitate harvesting of the cells therefrom.

In one embodiment, the movable portion comprises a partition. The partition may be positioned within a compartment of the reactor including the fixed bed. The apparatus may further include an expandable retainer for retaining the partition in the first position in a non-expanded condition of the retainer and the second condition in an expanded condition of the retainer.

A plunger may be provided. The plunger may be adapted for moving the partition from the first position to the second position, which plunger may be connected to the partition. The partition may include a first portion external to a compartment of the reactor comprising the fixed bed and a second portion within the compartment. The reactor may comprise a sealed container, and may comprise a flexible outer wall. A first compartment of the reactor may include the fixed bed and a second compartment may be provided for circulating fluid through the first compartment. The reactor may also comprise a roller bottle.

A further aspect of the disclosure pertains to an apparatus for processing cells. The apparatus comprises a container including a media compatible for cell growth and a partition associated with an interior compartment for the cells, the partition being movable from a first position for providing the compartment with a first volume to a second position providing the compartment with a second volume greater than the first volume.

The media may comprise a packing material in the compartment. The partition may form a lower portion of the compartment in the second position. The container may include an endwall, and the partition may be closed to the endwall in the first position than in the second position. An expandable retainer may be provided for retaining the partition in the first position in a non-expanded condition of the retainer and the second position in an expanded condition of the retainer. The expandable retainer may comprise a spring. A plunger may be provided for moving the partition from the first position to the second position, which plunger may be connected to the partition. The partition may include a first portion external to a compartment of the reactor including the fixed bed and a second portion within the compartment. An exterior compartment may also be provided for circulating fluid through the interior compartment. The partition may be generally annular.

A further aspect of the disclosure relates to an apparatus for processing cells. The apparatus comprises a container including a sidewall forming an interior for receiving a fluid, and an expandable compartment positioned within the interior of the container including a fixed bed for the cells. The expandable compartment may be surrounded by an exterior compartment in the interior of the container, and may surround an interior compartment. The sidewall may be at least partially flexible.

The apparatus may further include a vibrator. The apparatus may further include a device for circulating fluid within the reactor, such as a magnetic stirrer. The device or stirrer may be in a compartment of the reactor. The apparatus may include a plurality of cells. The apparatus may further include a release agent for detaching cells from a fixed location.

In a further aspect of the disclosure, an apparatus for processing cells using a liquid, comprises a reactor including a bed for growing the cells, a vibrator for vibrating the bed, and a drain for draining the fluid from the reactor to create an air-liquid interface within the bed. In one embodiment, the vibrator comprises a vibrating table for supporting the reactor. The bed may comprise a fixed bed, and the reactor may include a partition movable from a first position corresponding to a packed condition of the fixed bed to a second position corresponding to a depacked condition of the fixed bed, whereby movement of the partition expands the fixed bed to facilitate harvesting of the cells therefrom.

Still another aspect of the disclosure relates to a method of processing cells in a fixed bed reactor. The method comprises depacking the fixed bed and, after depacking, harvesting cells from the reactor. The harvesting step may comprise delivering a release agent to the reactor, vibrating the reactor, tapping the reactor, or combinations thereof. The depacking step may comprise expanding a compartment including the fixed bed of the reactor. The depacking step may comprise moving a partition supporting a packing material of the fixed bed. The depacking step may comprise lowering the partition.

A further aspect of the disclosure relates to a method of processing cells using a reactor including a bed having an air-liquid interface. The method comprises vibrating the bed. The step of vibrating the bed may comprise vibrating the reactor including the bed. The vibrating step may comprise placing the reactor on a vibrating table. The vibrating step may comprise tapping the reactor. The method may further include the step of moving the air-liquid interface during the vibrating step. The method may further include the step of the step of rinsing the bed, and then repeating the vibrating step. The method may further include the step of rotating the reactor during the vibrating step.

Yet another aspect of this disclosure pertains to a system for processing cells attached to a carrier in a fluid. The system comprises a container for receiving the cells, the carrier, and the fluid, said container including at least one port for releasing the fluid, a vibrator for vibrating the container, and a filter associated with the port. The filter may be adapted for passing the cells but not the carrier.

The system may further include a pump for increasing or decreasing pressure in a headspace in the container above the fluid. The system may further include an effluent line for passing fluid from the container through the filter. The port may comprise a multi-position drain, and the filter may comprise a flexible material surrounding the drain and adapted for allowing fluid to pass but not the carrier. The flexible material may comprise a mesh material.

Still another aspect of the disclosure pertains to an apparatus adapted for culturing cells on a carrier. The apparatus comprises a vessel including a drain having a drain opening larger than the carrier and a filter arranged for allowing fluid to pass into the drain opening but not the carrier. The filter may comprise a flexible material surrounding the drain opening. The flexible material may comprise a mesh.

Further to the disclosure, the aspect of a method for processing cells attached to a carrier in a fluid is described. The method comprises providing a container for receiving the cells, the carrier, and the fluid, said container including at least one port for removing the fluid, vibrating the container to detach the cells from the carrier, and filtering the carrier from the fluid removed from the vessel, such that the detached cells are removed with the fluid, and the carrier is not removed with the fluid. The filtering step may comprise removing fluid through the port and passing the fluid through a filter with a pore size smaller than the carrier and larger than the cells. The method may further comprise the step of pressurizing the container to remove the fluid. The pressurizing step may comprise providing a pump in communication with the container and applying a pressure in a headspace above the fluid. The vibrating and the pressurizing steps may be performed simultaneously.

A further aspect of the disclosure is a kit for use in connection with bioprocessing. In one embodiment, the kit comprises a sterilized first container including a first interior; a sterilized second container connected to the first container, said second container including a second interior, said second container including an additive within the second interior of the second container for being added to the first container; a removable barrier between the first and second containers for confining the additive to the second container; and a package for containing the first and second containers.

The barrier may comprise a removable clamp. The additive may be immiscible in a fluid. The first container may be a bioprocess vessel, such as a bag (which may include a mixer).

Another aspect of the disclosure relates to a kit for processing cells in connection with a fluid. The kit comprises a sterilized first container including a first interior, a sterilized second container connected to the first container, said second container including a second interior, an additive within the second interior of the second container, said additive being immiscible with the fluid, and a removable barrier between the first and second containers.

The additive may comprise a material adapted for carrying cells being grown. A mixer may be provided in the second container. The second container may be external to the first container.

A further aspect of the disclosure pertains to a kit for processing cells in connection with a fluid. The kit comprises a sterilized first container including a first interior having a mixer, a sterilized second container connected to the first container external to the first interior, said second container including a second interior, an additive within the second interior, and a removable barrier between the first and second containers.

The disclosure also pertains to a system for processing cells attached to a carrier in a fluid comprising any container disclosed herein, including the carrier and the fluid, and a vibrator for vibrating the container. A filter comprising pores of a size larger than the cells for filtering cells from the fluid and smaller than the carrier may also be provided, as may a pressure source for pressurizing the first container.

This disclosure also pertains to a method of providing a bioprocess system for use with a fluid. The method comprises attaching a first container to a second container, the second container including an additive immiscible with the fluid, sterilizing the attached first and second containers together, and packaging the sterilized first and second containers for transport. The packaging step may comprise providing a third container for surrounding the attached first and second containers and barrier. The method may further include the step of providing the first container with a mixer. The method may also include the step of unpackaging the first and second containers, removing a barrier to deliver the additive to the first container, adding a fluid to the first container, mixing the fluid, and recovering the fluid. The step of growing cells in the fluid may also be performed, and the recovery step may comprise passing the fluid from the first container through a filter adapted to allow the cells to pass while preventing the additive from passing from the first container. The method may further include pressurizing the first container during the recovery step, and/or vibrating the first container before or during the recovery step.

BRIEF DESCRIPTION OF THE DRAWINGS

FIGS. 7-8 illustrate details related to methods of using the disclosed inventions;

FIGS. 10, 10a and 11 show a further embodiment according to the disclosure;

DETAILED DESCRIPTION

Figure 1:
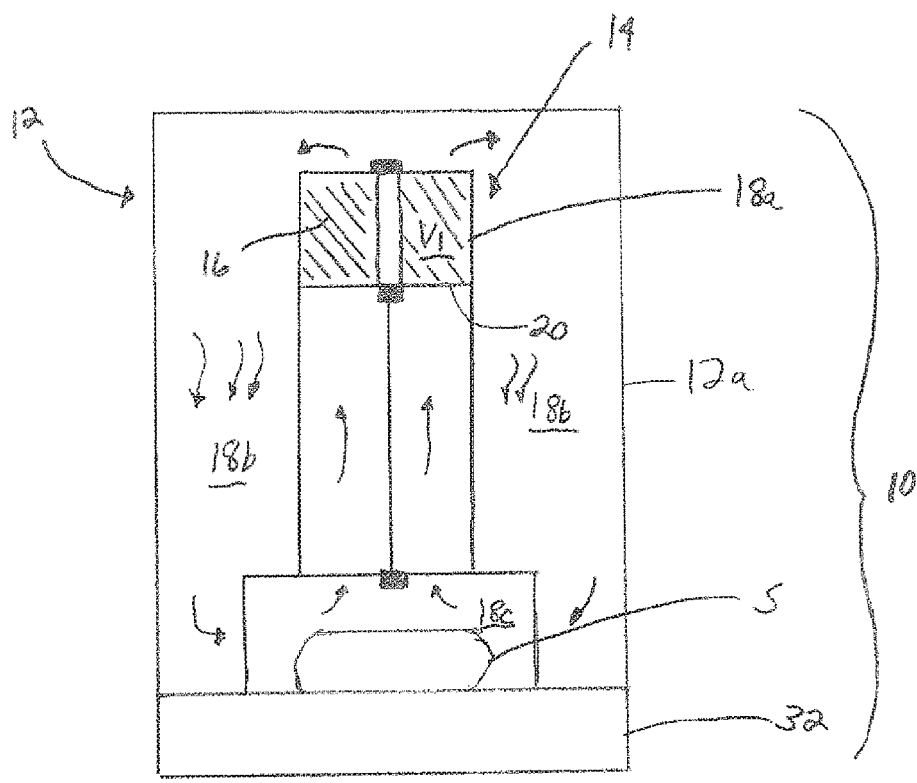
FIG. 1 is a schematic illustration of a first embodiment of a culturing vessel according to the disclosure.

Reference is now made to FIG. 1, which illustrates a system 10 for processing cells. In one embodiment, the system 10 includes an apparatus for growing cells in the form of a reactor 12. The reactor 12 may comprise a rigid or flexible container (e.g., a bag) arranged for receiving and containing a fluid, and may be adapted for being used only once (which avoids the need for cleaning procedures and the associated expense). In any case, the container forming the reactor 12 may be sealed from the ambient environment during use in order to maintain a sterile interior condition for growing cells in the optimal manner.

The reactor 12 includes a wall 12a forming an interior with a packed or fixed bed 14 comprised of a packing material 16 (such as fibers, beads, spheres, or the like) for promoting the adhesion and growth of cells. The material 16 is located in a compartment 18a within the interior of the reactor 12, which compartment may comprise an upper portion of a hollow, vertically extending tube. A second compartment 18b is provided within the interior of the reactor 12 for conveying fluid to and from the material 16 of compartment 18a at least partially forming the fixed bed 14. Typically, the packing material 16 should be arranged to maximize the surface area for cell growth, with 1,000 square meters being considered an advantageous amount of surface area (which, for example, may be achieved using medical grade polyester microfibers as the packing material 16).

A circulation device, such as for example a magnetic stirrer S, may also be provided for moving fluid in the reactor 12 through the fixed bed 14, but an external pump (not shown) could also be used. The stirrer S may be provided in a third compartment 18c of the reactor 12 and in fluid communication with the first and second compartments 18a, 18b. The resulting flow may be from the bottom to the top of the reactor 12, as indicated by the action arrows in FIG. 1. Details of one possible approach to forming a reactor 12 in this manner may be found in U.S. Pat. No. 8,137,959, the disclosure of which is incorporated herein by reference.

Figure 2:
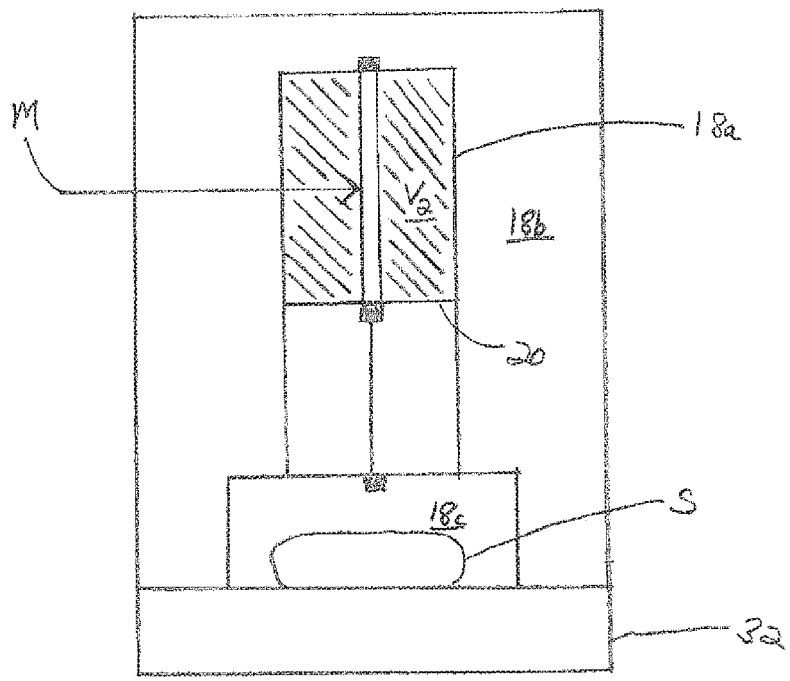
FIG. 2 is a schematic illustration of the FIG. 1 embodiment.

As can be best understood with reference to FIGS. 1 and 2 together, the reactor 12 may be adapted such that the packing material 16 of the fixed bed 14 may be expanded, or "depacked," from a packed condition. Thus, as shown in FIG. 1, the reactor 12 is associated with an expandable portion, which may comprise movable partition 20 for dividing the compartment 18a into two sections. In the illustrated embodiment, this partition 20 provides support for the packing material 16 within the compartment 18a forming the fixed bed 14, which again may comprise a hollow, vertically extending tube. The partition 20 may be designed to have an outer diameter less than that of the tube 18a, and is also permeable to fluid.

In a first state for growing cells, the partition 20 is initially positioned to create a first volume V1 in the corresponding compartment 18a including the densified packed material 16, which in such condition may provide optimal conditions for fluid, heat, and mass transport through the bed 14. When harvesting of the cells is desired, the partition 20 may be moved to expand the first volume of the compartment 18a forming the packed bed 14 to a second, greater volume V2 (and possibly without opening the reactor 12), and thereby allow the packing material 16 to expand or depack. In this condition of the material 16, the cells may then be more readily detached for harvesting, which as noted above may be achieved using a chemical agent alone or in combination with other techniques, as outlined in further detail in the following description.

Figure 3:
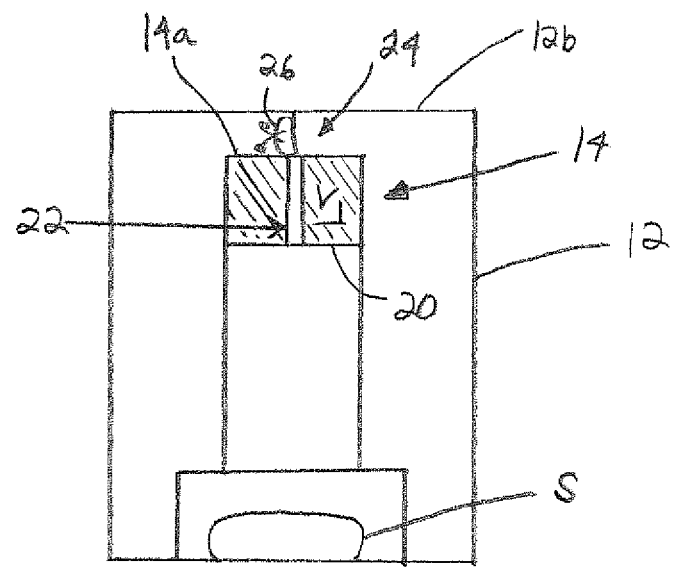
FIGS. 3-6 are schematic illustrations of alternate embodiments.
Figure 4:
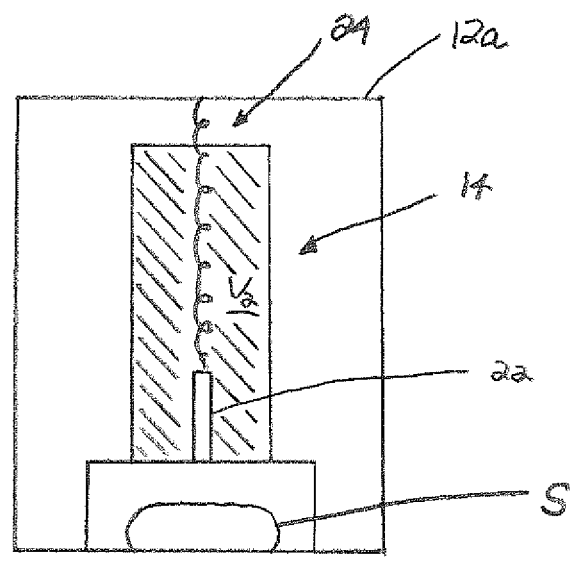

FIGS. 3-6 illustrate various embodiments for achieving the depacking function. In FIGS. 3 and 4, the partition 20 is connected to a spacer 22, which may be positioned adjacent to or abut the permeable upper wall 14a adjacent the bed 14 to define the first or packed condition. An expandable retainer 24, such as for example a coil spring, may extend between the partition 20 and a fixed structure, such as the upper wall 12b of the reactor 12.

When the retainer 24 is in a compressed or non-expanded condition (e.g., the compressed condition of the spring), the partition 20 thus retains the material 16 of the bed 14 in a packed condition. When harvesting is desired, the retainer 24 may be allowed to expand (such as in the case of the spring by detaching an associated holder 26, such as by cutting or severing). As can be understood with reference to FIG. 4, this expansion allows the partition 20 to move and expand the volume of the compartment 18a and thereby depack the material 16 of the bed 14.

Figure 5:
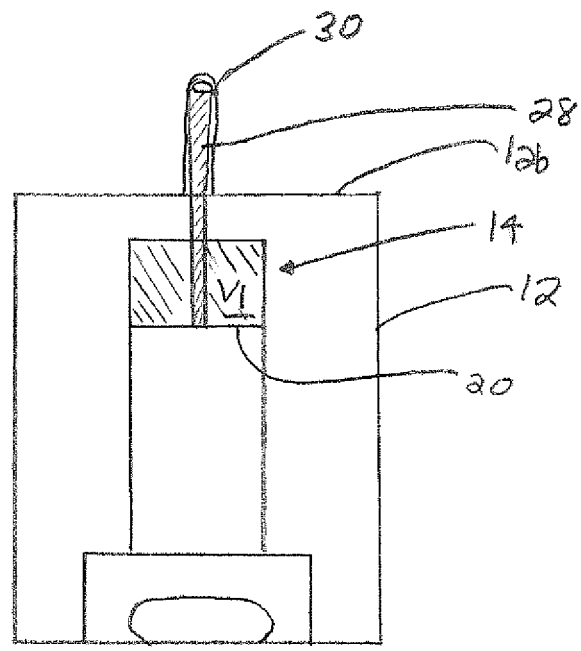
Figure 6:
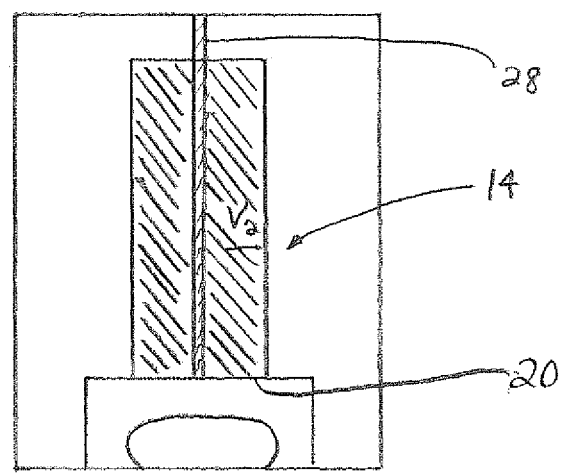

The embodiment in FIGS. 5 and 6 achieves a similar end result, but the manner of moving the partition 20 is different. In this embodiment, the partition 20 is connected to a plunger 28, which may pass through a wall (such as the upper wall 12a) of the reactor 12. Activating the plunger 28 moves the partition 20 such that the bed 14 changes from the first or packed condition (FIG. 5) to the expanded condition (FIG. 6). As should be appreciated, one advantage of this embodiment is that the plunger 28 may be returned to the position associated with the packed condition once harvesting proceeds, and then re-activated to the unpacked condition. To maintain the sterile conditions, a seal 30 (including possibly a sleeve) may associate the plunger 28 with the reactor 12.

As noted above, a chemical agent, such as trypsin, can be used during harvesting. In a further embodiment, and with reference to FIGS. 7 and 8, the packing material 16 may be subjected to vibrations to facilitate cell detachment. This may be done by placing the entire reactor 12 on a vibrating table 32, or by simply tapping the reactor 12. Subjecting the packing material 16 to vibrations may be done either alone or in combination with the application of a chemical agent. The vibrations may be applied in the expanded or non-expanded condition of the bed 14. In the case of harvesting with combined vibrations and chemical agent, the vibrating may be done prior to, during, or after the introduction of any chemical agent.

EXAMPLES

Figure 7:
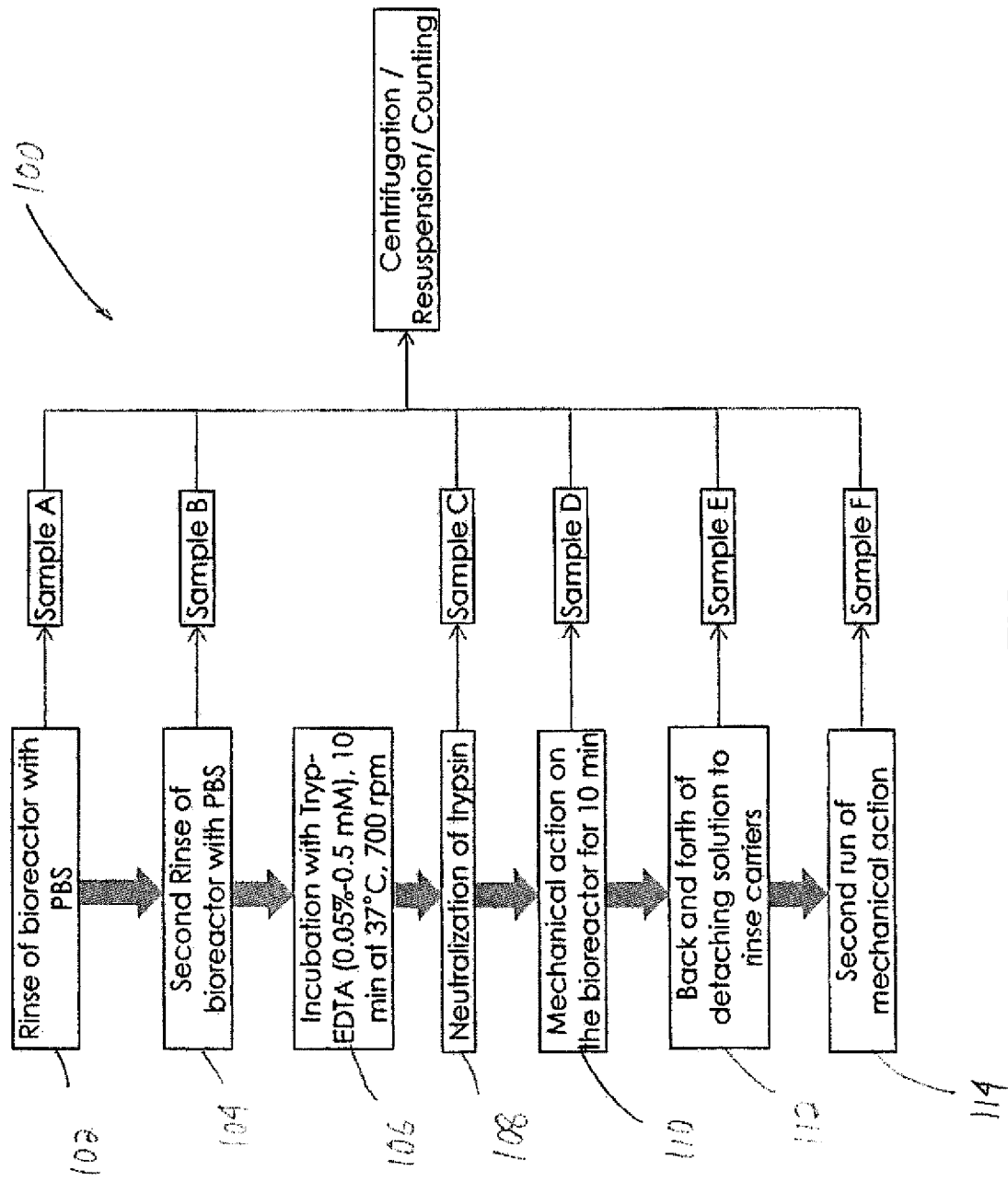

With reference to FIGS. 7 and 8, one possible manner of implementing the invention is described. FIG. 7 illustrates the flow of steps in a harvesting method 100, which includes a rinsing step 102 with phosphate buffered saline (PBS), followed by an optional second rinse 104, an incubation step 106, a neutralization step 108, and then the application of a mechanical action to the reactor at step 110, such as by applying vibrations to dislodge the cells. After rinsing again at step 112, mechanical action is applied again, as indicated at step 114. FIG. 8 indicates the various yields of cells harvested as a result of sampling done at each step in the process, and indicates that the first mechanical action step increases the yield remarkably.

Another example involves emptying fluid from the reactor, and then adding a rinsing solution (such as PBS preheated to 37 degrees Celsius). The rinsing solution is circulated through the fixed bed, and the reactor emptied. An enzymatic detachment solution (e.g., trypsin) is then circulated through the bed. The reactor is then placed on a vibrating table for 10 minutes at a frequency of 50 Hz and amplitude of about 1 millimeter. The fluid may then be drained as part of the recovery step, either by halting the vibrating while partially draining the fluid, or by forming a moving air-liquid interface during the vibration (see line M in FIG. 2, indicating this interface at the middle of the bed). Neutralization of the enzymatic solution may be completed once the reactor is emptied.

Figure 9:
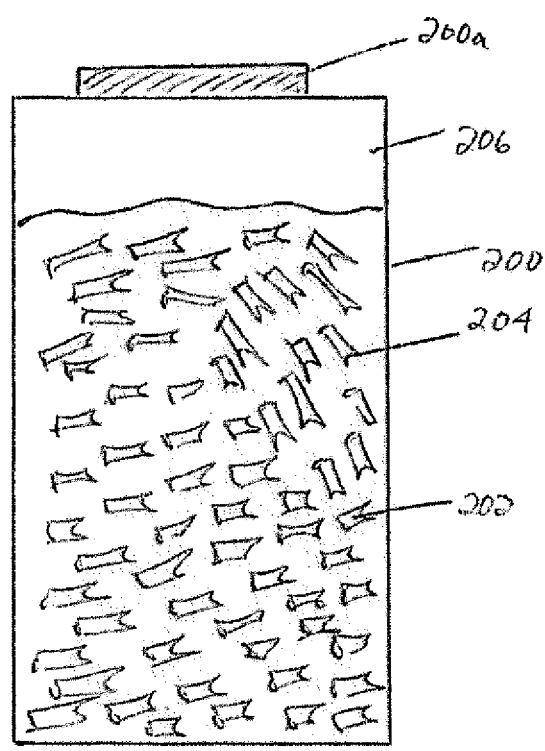
FIG. 9 illustrates still another embodiment.

FIG. 9 further illustrates that depacking of the bed 14 may occur by placing the unpacked packing material 16 in a vessel 200 separate from the reactor 12. This may be achieved by placing the individual carriers 202 forming the fixed bed 14 in the reactor 12, into the vessel 200 and in solution with a detachment agent 204, such as trypsin, and forming a headspace 206 (such as air). The container 200 may comprise a closed container, such as a roller bottle, having a removable cap 200a. The container 200 may also be subjected to vibrations in order to facilitate cell detachment from the carriers 202.

Reference is now made to FIGS. 10 and 11, which illustrate a further embodiment of a recipient 1 suitable for use as a bioreactor. The recipient 1 for cell cultivation has an inner space 2 containing packing 3. When the recipient is to be used for cell culture the packing 3 should be compatible with cell growth. The inner space 2 may have any shape, but in the disclosed embodiment has an annular volume delimited by:

- an outer tubular wall 4 having a first outer end 41 and a second outer end 42 and a longitudinal wall 43 extending in longitudinal direction, referred to by arrow 44. The outer tubular wall 4 delimits an outer boundary of the annular volume in longitudinal direction 44;
- a first and a second closure 61, 62 delimiting and closing the annular volume at the first outer end 41 respectively the second outer end 42 of the outer tubular wall 4;
- an inner elongate wall 5 having a first outer end 51 oriented towards the first outer end of the outer tubular wall, and a second outer end 52 oriented towards the second outer end of the outer tubular wall 4. The inner elongate wall 5 is positioned within the outer tubular wall 4. The inner elongate wall 5 extends in longitudinal direction 44 and delimits an inner boundary of the annular volume, the inner boundary being encompassed by the outer boundary.

The second outer end 52 of the inner elongate wall 5 coincides with the second closure 62. As an example, the outer tubular wall is provided by a cylindrical outer tubular element 40. The inner elongate wall 5 may be provided by a solid inner cylindrical element 50, such as a cylindrical rod. The outer tubular element 40 is a cylindrical tubular element, and has a central axis 45, parallel to the longitudinal direction. The inner cylindrical element 50 and the outer tubular element 40 may be coaxially mounted.

The first outer end of the inner cylindrical element 50 may comprise a coupling element 53 to couple the inner cylindrical element 50, and by means of the closures 61 and 62 being fixed to the inner cylindrical element 50 and the outer tubular element 40, the outer tubular element 40 as well, to a drive mechanism, e.g. a motor of the bioreactor. The second closure 62 is provided with a connector, suitable to couple the recipient to a medium or gas source, for providing and/or extracting medium and/or gas to and/or from the inner space 2. This connector, or alternatively additional connectors, may be provided to the first closure 61 or the second closure 62.

The inner space 2 is at least partially filled with packing 3. As an example the packing may be mineral carriers such as silicates, calcium phosphate, organic compounds such porous carbon, natural products such as chitosan, polymers or biopolymers compatible with cell growth. The packing may comprise woven or non-woven microfibers of a polymer or any other material compatible with cell growth. The packing can also be provided as a single piece of material with pores and or channels.

Optionally, the packing may have a porosity P in the range of 50% to 98%. The term porosity P is the volume of air present in a given volume of the material, and expressed as percentage of the given volume of the material. The porosity can be measured by measuring the weight Wx per volume of the porous material, and using the formula:

$$P=100-(1-Wx/Wspec)$$

wherein Wspec is the specific weight of the material. The porous material may be one solid unit of material, or may be a plurality of individual units, such as grains, chips, beads, fibres or fiber agglomerates.

Upon moving the recipient 1, the packing (in particular the porous material) may rest in a fixed relative position to the recipient. The recipient 1 is to be rotated about its axis 45, optionally at a rotational speed of between 0.1 and 25 rotations per minute.

As best visible in the radial cross-section portion of FIG. 10a, the inner space is partially filled with cultivation medium, such as cell cultivation medium 15. As an example, the liquid level 18 at least contacts the inner elongate wall 5, which is partially submerged in the medium 15. The part of the packing 3 positioned under the liquid level 18 is wetted by the cultivation medium, such as cell cultivation medium. The packing 3 positioned above the liquid level 18 is in contact with the gas or air present in the inner space 2. When the recipient is rotated in one direction about the axis 45, e.g., clockwise rotated as indicated by arrow 17, the cultivation medium, such as cell cultivation medium 15 rotates in opposite, say anti-clockwise direction (indicated by 19) relative to the packing 3. The cultivation medium, such as cell cultivation medium 15 is passed through the complete packing 3 according to a plug flow. Upon rotation, e.g. clockwise, of the recipient, the cultivation medium, such as cell cultivation medium forces the gas or air 16 at the leading edge 20 of the plug flow to displace anti-clockwise. At the tailing edge 21 of the medium 15, an optionally limited depression is created, causing gas or air 16 to be sucked towards the trailing edge. As such the medium 15 and the gas or air 16 passes through the complete packing 3.

As shown in FIG. 11, the outer tubular wall 4 may be provided by an outer tubular element 240. The inner elongate wall 5 may be provided by an elongate cylindrical tubular element 250. The outer tubular element 240 and the elongate cylindrical tubular element 250 are fixed to two removable closures 261 and 262. The first closure 261 is provided with a coupling element 253 for coupling the recipient to a driving means for rotating the recipient along an axis in longitudinal direction 44. The first closure 261 further comprises a connector 263 for connecting the inner space 2 to e.g. a flexible tube.

As an example, the outer tubular element may be a glass tube, having a length L of e.g. 110 mm and an inner diameter Do of e.g. 135 mm. The inner elongate element may be a polyvinylidenefluoride (PVDF) tube having an outer diameter Di of e.g. 88.9 mm. The outer ends of the inner elongate element, hence of the inner elongate wall, coincide with the closures 261 and 262. The closures may be stainless steel or PVDF annular discs, which may be attached to the inner and outer element using silicone. The first closure 261, which may be provided with a connector 263, has a coupling element 253, having an outer diameter Dce of e.g. about 35 mm.

As noted above, the inner space 2 is at least partially filled with packing 3. As an example, the packing may be identical or similar to the packing in the embodiment of FIG. 10. With reference to FIG. 11, it can be understood that the packing may be fixed, and contained within a compartment defined by a partition 270, which in the illustrated embodiment may be annular. The partition 270 may be arranged to move within the space 2 between a packed condition (as shown) and an unpacked condition (not shown) to facilitate cell recovery. The movement may be caused by an actuator, such as plunger 280. The recipient 1 may also be rotated with the packing 3 in the unpacked condition to circulate a suitable release agent through the material, and may also be vibrated to facilitate cell detachment.

Figure 12:
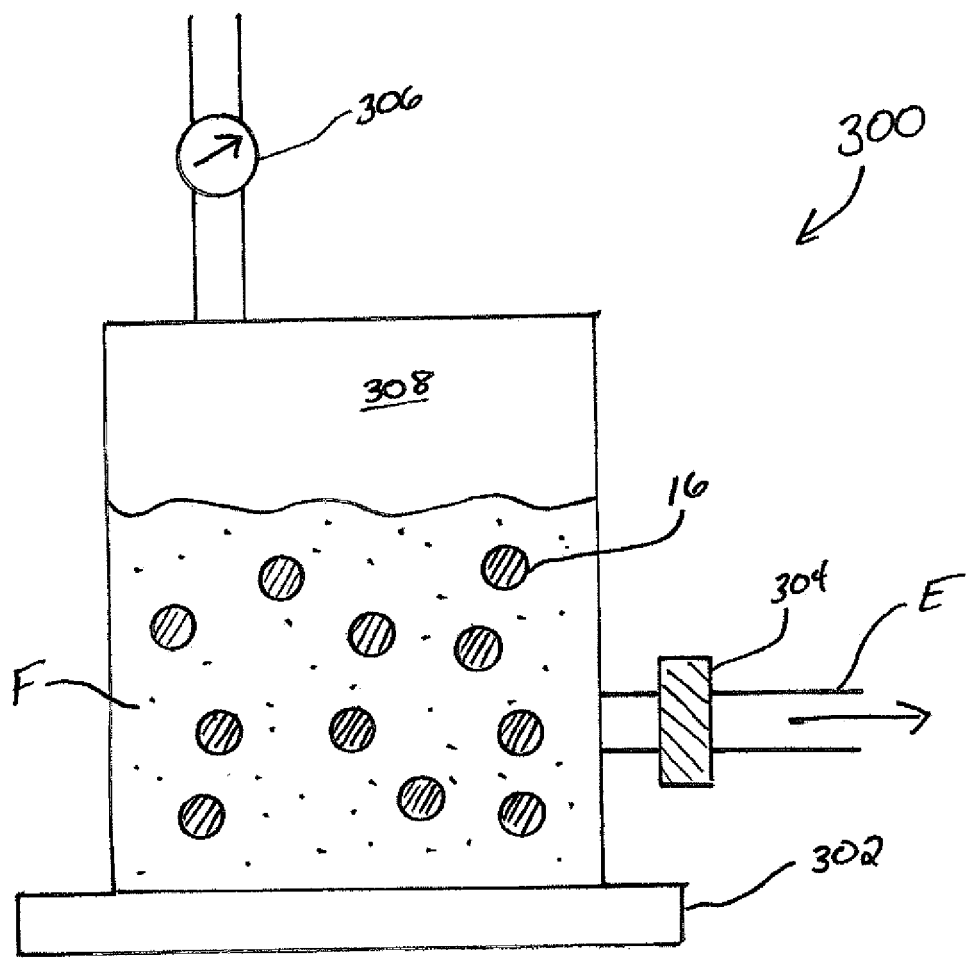
FIGS. 12-14 illustrate additional embodiments according to the disclosure.

Turning to FIG. 12, a further embodiment of a system for detaching cells is disclosed. In this embodiment, a vessel 300 is provided for retaining the cell growth compatible material 16 which may be suspended in a fluid F. The vessel 300 may be a cell culture or bioprocess vessel, or may be a storage container for receiving the contents of a cell culture or bioprocess vessel after use. The fluid F within the vessel 300 may be media for cellular growth, water or other washing fluid, a chemical agent such as trypsin, or any combination thereof.

The material 16 may be in the form of microcarriers such as powders, grains, chips, beads, or fibers. This material 16 may form agglomerates, or may be in suspension in the fluid F. In one embodiment, cells to be harvested are at least partially attached to the material 16.

The vessel 300 may be subject to vibration for removal of the cells from the packing material 16. The vibration may be at low amplitude and high frequency to maximize efficiency. As before, this vibration may be accomplished by placing the vessel 300 on a vibration table 302, or by manually vibrating the vessel 300. As the packing material 16 is vibrated, the cells begin to become dislodged from the material 16. The cells may then become suspended in the fluid F, independent of the material 16.

The vessel 300 may further include a filter 304, which may be used in connection with an effluent line E. The filter may be sized so as to allow cells, including those detached from the material 16, to pass through, but prevent the passage of the material 16. In this case, the effluent line E, downstream of the filter 304, would include harvested cells, separate from the material 16.

Additionally, the vessel 300 may include a pressurizing device such as a pump 306. This pump 306 may increase the pressure in a headspace 308 in the vessel 300 above the level of the fluid F. This increase in pressure above the fluid F may cause the fluid to exit the vessel through the effluent line E, and consequently the fluid level to lower. This pressurization and lowering of the fluid level may occur independently of or simultaneously with the application of vibration but, as discussed above, there may be an advantage to having the vibrations concentrated at the air-liquid interface, if possible.

Figure 13:
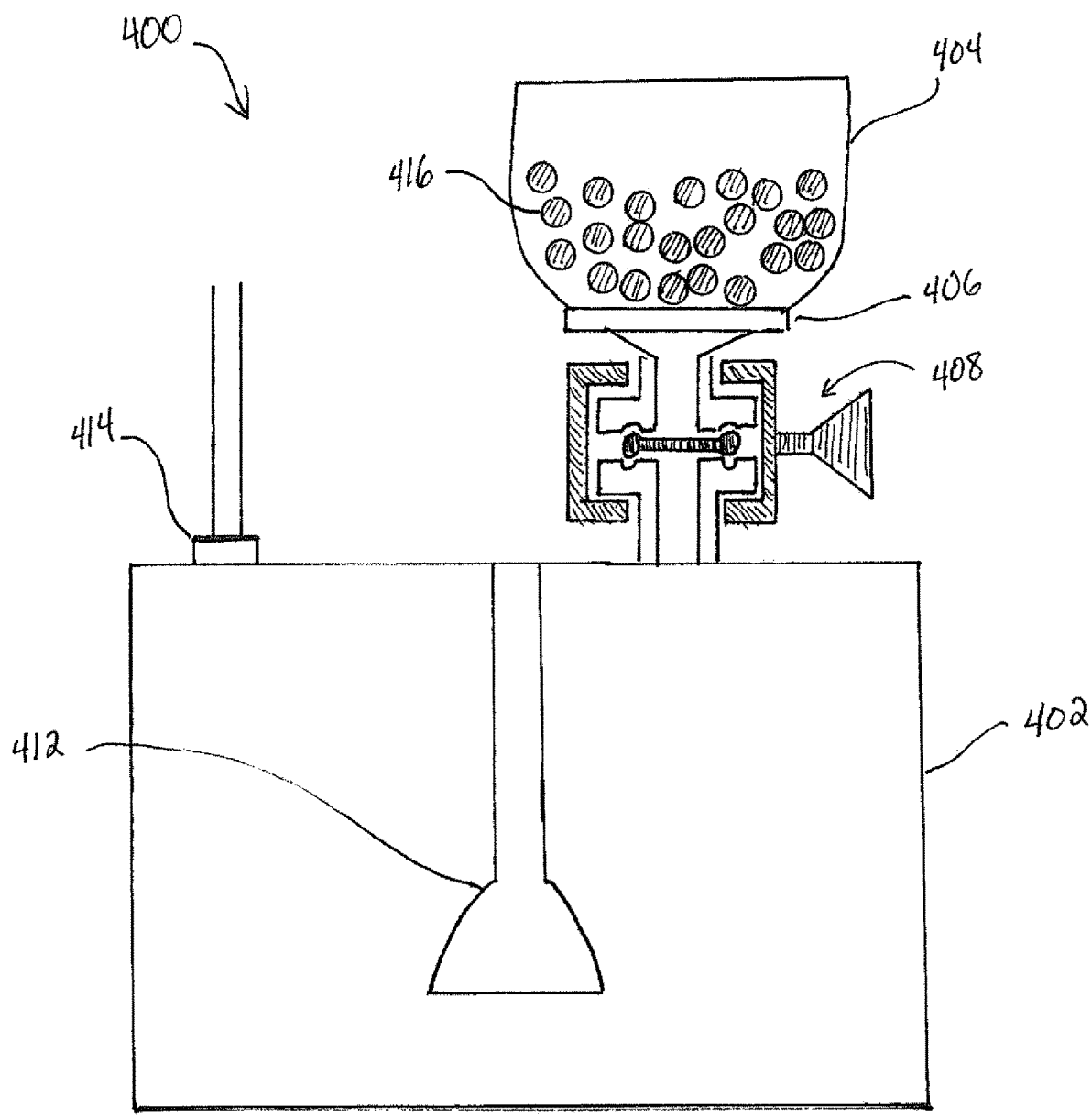

With reference to FIG. 13, a system 400 is disclosed which may be used to transfer a material from one container to another in a sterile manner. In one embodiment, the system may comprise a first container 402, which may be in the form of a bioprocessing container, such as a flexible bag, or an at least partially rigid vessel. The first container may include a mixer such as an impeller, paddle 412, or the like, and may further include a port 414 for the addition of a fluid. In one embodiment, the first container 402 may be of the type described in U.S. Patent App. Pub. No. 2010/0015696 or U.S. Pat. No. 7,384,027, the disclosures of which is incorporated by reference.

The system 400 may further include a second container 404 that may be attached to the first container 402, either permanently or temporarily. The second container 404 may have a volume substantially less than the first container 402, and may be about 10% or less of the volume of the first container.

The second container 404 may include an additive 416 that may be added to the first container 402. The additive 416 may be any material that may be added to the first container 402 in a sterile manner, such as a nutrient for cellular growth, a chemical additive, or a material for promoting adherent cell growth. In the case of the additive 416 being a cell adherent material, it may be in any of the forms previously described, such as a carrier or microcarrier in the form of a powder, grains, chips, beads, fibers, or fiber agglomerates. The additive 416 may be immiscible with a fluid in the first container 402, and may be immiscible with any aqueous fluid, such as the liquid culture media.

In one embodiment, the system 400 further includes a barrier or seal between the first container 402 and the second container 404. The barrier may be removable, so as to allow passage of the additive 416 from the second container 404 to the first container 402. As illustrated in FIG. 13, the barrier may be in the form of a removable retainer, such as a clamp or clip 406, which prevents the additive 416 from escaping the second container 404.

The first container 402 and the second container 404 may be permanently connected, such as through a seamless material connecting the two containers. Alternatively, the system may include a connection fitment 408 for connecting the first container 402 to the second container 404. The connection fitment 408 may be in the form of a cleat for retaining one or more extensions on the first or second containers 402, 404, or a valve between the first and second containers. One or more filters (not shown) may be used in connection with the connection fitment or any other port with access to any part of the system 400.

In practice, the second container 404 may be filled with the additive 416 and connected to the first container 402, as in any manner previously discussed. The components may be sterilized individually and then connected in a sterile manner, or the entire system 400 may be connected and then sterilized simultaneously (including any additive). In any case, the connected first and second containers 402, 402 create a closed system which is sterilized. This closed system may then be used in any environment, whether sterile or not, while not affecting the sterility within the system 400.

Figure 14:
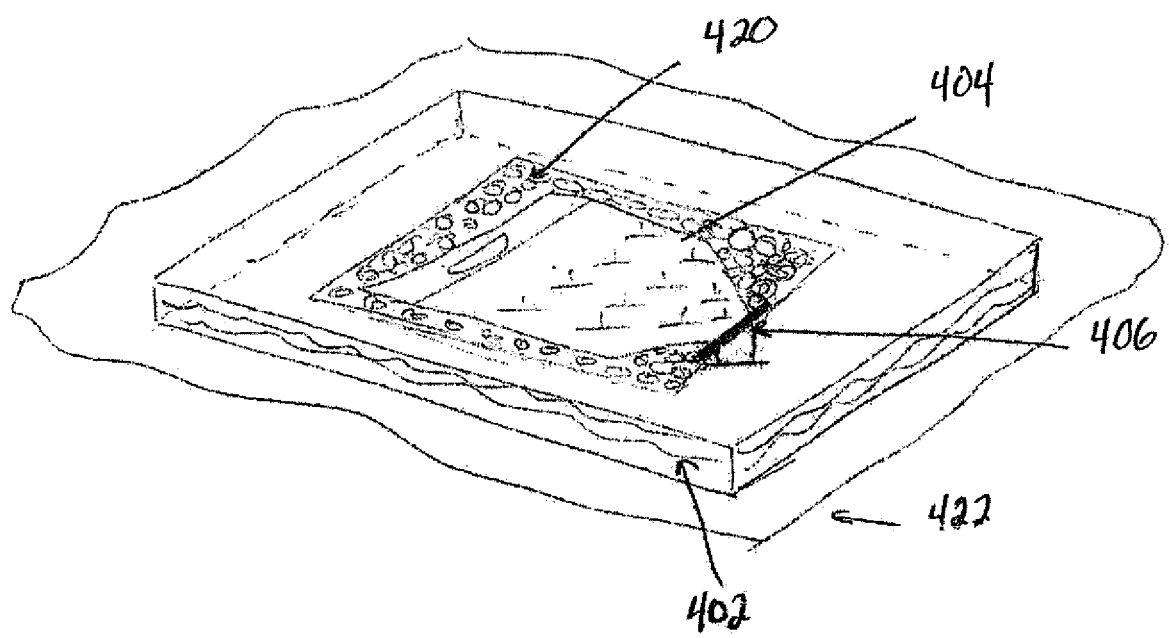

The sterilized system 400 may be shipped as a single unit or kit as illustrated in FIG. 14. One or more of the first and second containers 402, 404 may be covered in a protective layer such as a cushion 420 to protect against damage. The system 400 may also be surrounded by a packaging layer such as bag 422 for transportation as a single unit.

Figure 15:
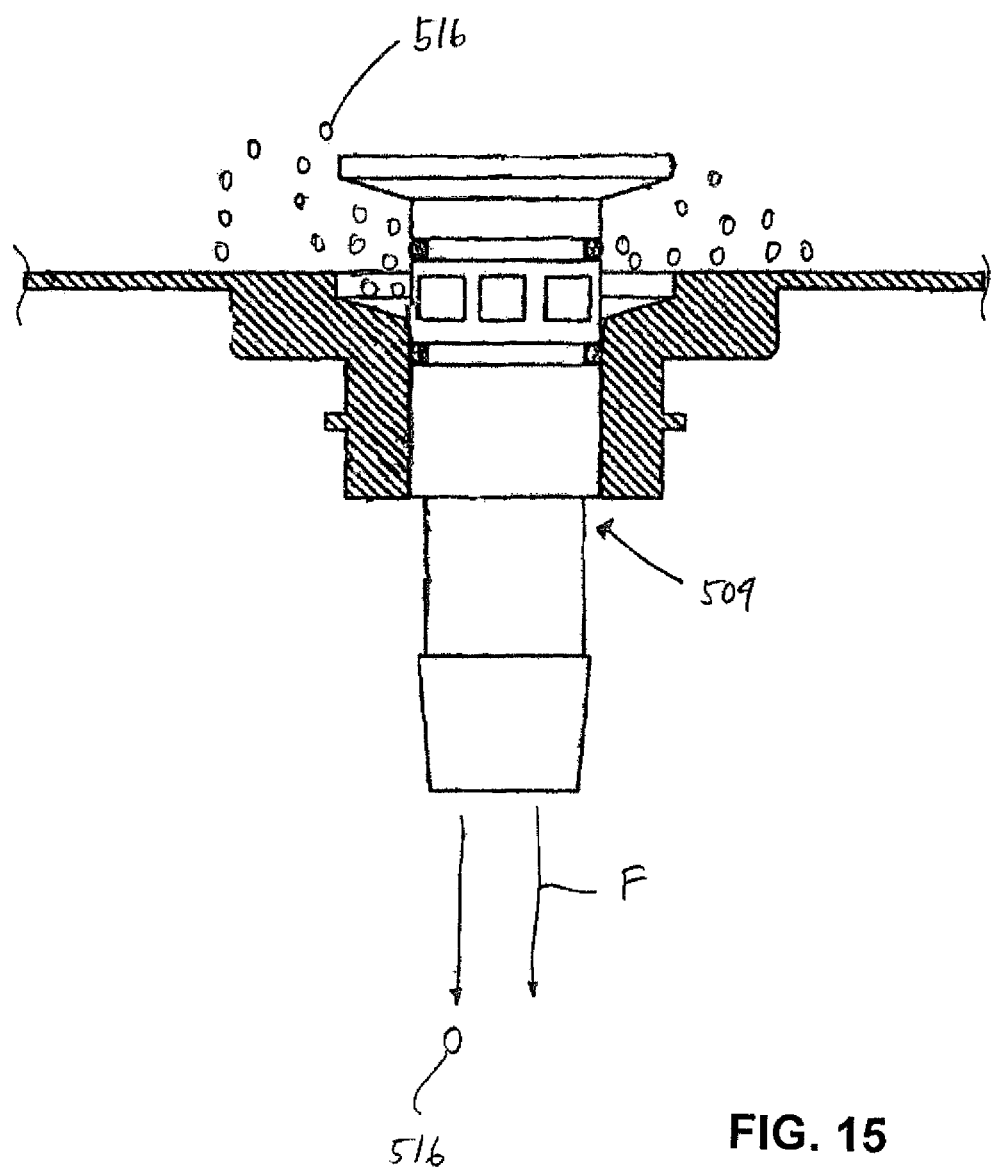
FIGS. 15-16 illustrate still further embodiments according to the disclosure.
Figure 16:
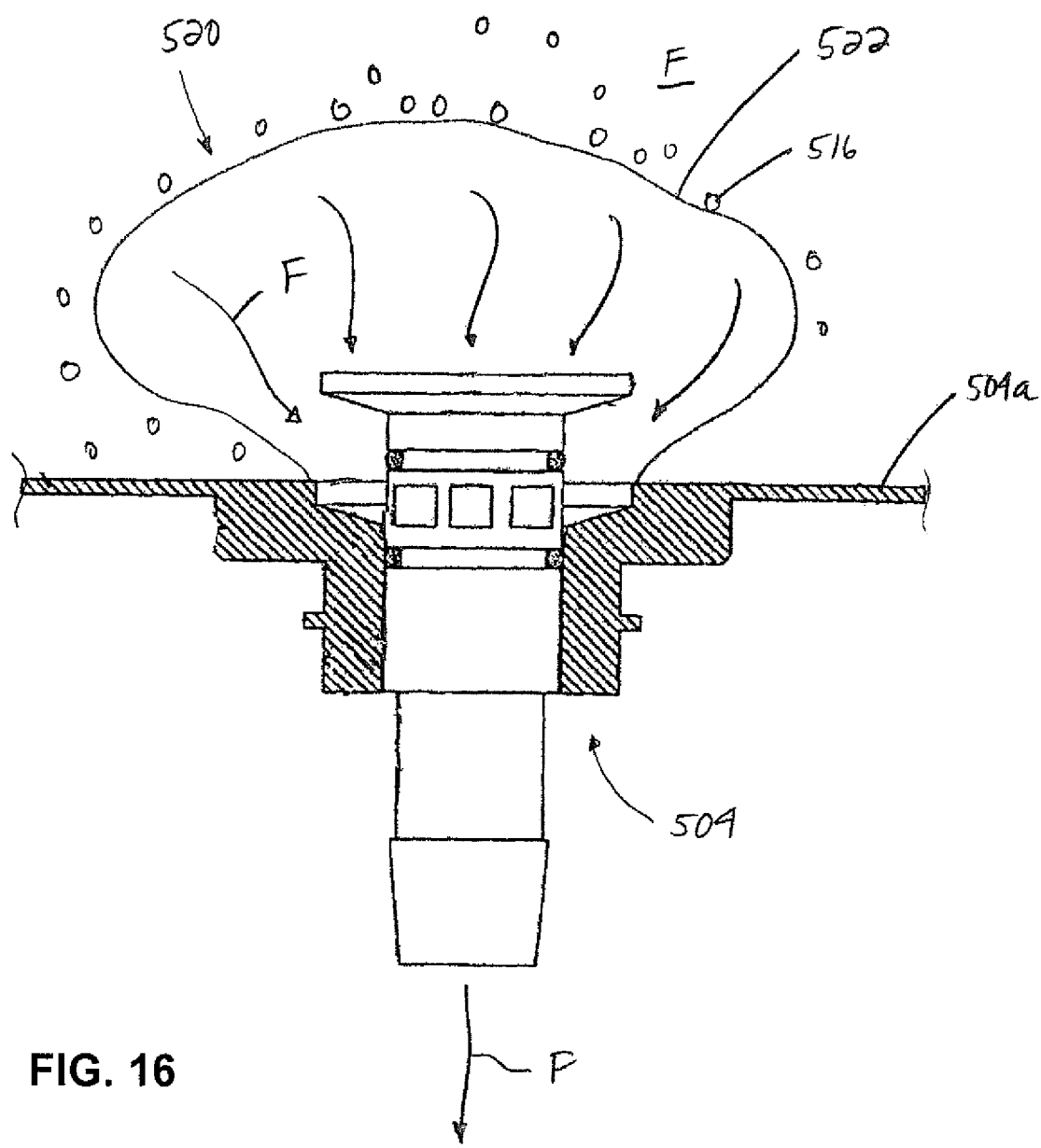

Referring now to FIGS. 15 and 16, it can be appreciated that a system 500 may include a vessel 502 having a multi-position drain 504, including a closed position for preventing flow and sealing the inner compartment of the vessel 502, and an open position (as illustrated) for allowing flow to proceed. The positions may be manually or automatically adjusted, and such is unimportant for purposes of this disclosure. An example of such a drain may be found in U.S. Patent Application Publication No. 2012/0260608, the disclosure of which is incorporated herein by reference.

When a carrier for promoting adherent cell growth, such as beads 516, is present, it is desirable for this material to remain in the compartment of the container or vessel while the fluid F is recovered (including any cells). If a drain 504 is used for this purpose, it should be appreciated that the beads 516 or other material may crowd the drain opening serving as the outlet and prevent flow from proceeding in the desired manner. Depending on the relative sizes and shapes, which are not perfect among the material, the beads 516 may also escape with the effluent and necessitate an undesirable further filtering step.

Accordingly, one aspect of the disclosure is to associate the drain with a pre-filtering element 520 adapted to allow the fluid F to pass but retaining any adherent material or the like in the compartment of the vessel 502. In the illustrated embodiment, this element 520 comprises a flexible material in the form of a mesh 522 having openings sized for allowing the passage of the fluid, while keeping the beads 516 from passing. As should be appreciated, this arrangement of mesh 522 creates a permeable bag-like structure that forms a buffer zone between the drain opening associated with the interior compartment of the container and the compartment itself, and thus serves to promote the free flow of fluid. The flexible nature of the mesh 522 also allows for it to be easily manipulated from external to the vessel 502, such as by shaking or vibrating. This manipulation is especially simplified when the vessel 502 comprises a flexible mixing bag, which may include an opening for receiving a flange 504a forming part of the drain 504.

The foregoing descriptions of several embodiments made according to the disclosure of certain inventive principles herein are presented for purposes of illustration and description. The embodiments described are not intended to be exhaustive or to limit the invention to the precise form disclosed and, in fact, any combination of the components of the disclosed embodiments is contemplated. The term "flexible" as used herein in the context of the reactor refers to a structure that, in the absence of auxiliary support, may conform to the shape of the fluid contained in the reactor, as contrasted with a "rigid" structure, which retains a predetermined shape when the fluid is in the reactor. Modifications or variations are possible in light of the above teachings. For instance, while the partition 20 is shown as forming a lower portion of the bed 14, the movable portion could also be a top plate or sidewall. The embodiments described were chosen to provide the best illustration of the principles of the invention and its practical application to thereby enable one of ordinary skill in the art to utilize the invention in various embodiments and with various modifications as are suited to the particular use contemplated. All such modifications and variations are within the scope of the invention when interpreted in accordance with the breadth to which it is fairly, legally, and equitably entitled.

The invention claimed is:

1. An apparatus for processing cells, comprising:
a fixed bed reactor for the cells, the fixed bed reactor including a portion movable from a first position corresponding to a packed condition of a fixed bed to a second position corresponding to a depacked condition of the fixed bed, wherein the movable portion comprises a partition positioned within a compartment of the reactor including the fixed bed;
an expandable retainer for retaining the partition in the first position in a non-expanded condition of the retainer and the second condition in an expanded condition of the retainer; and
a vibrator for vibrating the fixed bed;
whereby movement of the portion expands the fixed bed to facilitate harvesting of the cells when the fixed bed is vibrated by the vibrator;
wherein the fixed bed reactor is sealed from an ambient environment during use in order to maintain a sterile interior condition for growing cells.

2. The apparatus of claim 1, wherein the expandable retainer comprises a spring.

3. The apparatus of claim 2, wherein the spring extends between the partition and a wall of the fixed bed reactor.

4. An apparatus for processing cells, comprising:
a fixed bed reactor for the cells having a fixed bed with a packed condition and a depacked condition, the fixed bed reactor including a partition adapted for moving from a first position contacting the fixed bed in the packed condition to a second position corresponding to the depacked condition of the fixed bed;
a vibrator for vibrating the fixed bed in the depacked condition; and
a stirrer in the fixed bed reactor for circulating fluid within the fixed bed in the packed condition;
wherein the fixed bed reactor is sealed from an ambient environment during use in order to maintain a sterile interior condition for growing cells.

5. An apparatus for processing cells grown in a packed fixed bed, comprising:
a fixed bed reactor including a movable partition positioned to achieve a depacked condition of the fixed bed;
a vibrator for vibrating the fixed bed in the depacked condition; and
a stirrer in the fixed bed reactor for circulating fluid within the fixed bed in the packed condition;
whereby movement of the portion expands the fixed bed to facilitate harvesting of the cells when the fixed bed is vibrated by the vibrator;
wherein the reactor is sealed from an ambient environment during use in order to maintain a sterile interior condition for growing cells in the optimal manner.

6. An apparatus for processing cells, comprising:
a fixed bed reactor for the cells, the fixed bed reactor including a portion movable from a first position corresponding to a packed condition of a fixed bed to a second position corresponding to a depacked condition of the fixed bed,
a vibrator for vibrating the fixed bed;
whereby movement of the portion expands the fixed bed to facilitate harvesting of the cells when the fixed bed is vibrated by the vibrator;
wherein the fixed bed reactor is sealed from an ambient environment during use in order to maintain a sterile interior condition for growing cells;
wherein the reactor comprises a roller bottle.

7. An apparatus for processing cells, comprising:
a fixed bed reactor for the cells, the fixed bed reactor including a portion movable from a first position corresponding to a packed condition of a fixed bed to a second position corresponding to a depacked condition of the fixed bed,
a vibrator for vibrating the fixed bed; and
a stirrer in the fixed bed reactor for circulating fluid within the fixed bed in the packed condition;
whereby movement of the portion expands the fixed bed to facilitate harvesting of the cells when the fixed bed is vibrated by the vibrator;
wherein the fixed bed reactor is sealed from an ambient environment during use in order to maintain a sterile interior condition for growing cells.

* * * * *